United States Patent
Zaslavsky et al.

(10) Patent No.: US 6,228,023 B1
(45) Date of Patent: May 8, 2001

(54) TISSUE PICK AND METHOD FOR USE IN MINIMALLY INVASIVE SURGICAL PROCEDURES

(75) Inventors: Ella Zaslavsky, Marblehead; Robert B. Stewart, Ipswich, both of MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/251,359

(22) Filed: Feb. 17, 1999

(51) Int. Cl.[7] ........................................ A61B 1/32
(52) U.S. Cl. ........................ 600/204; 600/206; 600/217; 606/1
(58) Field of Search ........................ 600/201, 204, 600/206, 210, 217, 235, 214, 104; 606/1

(56) References Cited

U.S. PATENT DOCUMENTS

| | | | |
|---|---|---|---|
| 5,403,342 | * | 4/1995 | Tovey et al. . |
| 5,437,266 | * | 8/1995 | McPherson et al. ................ 600/217 |
| 5,609,601 | * | 3/1997 | Kolesa et al. . |
| 5,865,791 | * | 2/1999 | Whayne et al. . |

OTHER PUBLICATIONS

Szabo, Zoltan, *Laparoscopic Suturing and Tissue Approximation*, in Minimally Invasive Surgery, Chapter 14:141–155 (Jane Pennington et al. eds., 1993).

Fine Science Tools, Inc., Catalog No. 11, p. 103 "Surgical Accessories: double–pronged pick for tissue, skin, etc.", 1996.

* cited by examiner

*Primary Examiner*—Jeffrey A. Smith
(74) *Attorney, Agent, or Firm*—Samuels, Gauthier & Stevens, LLP.

(57) ABSTRACT

A tissue pick for use during minimally invasive surgeries includes a tissue grasping member disposed at the end of the tissue pick. The tissue grasping member may be rotated, articulated at an angle, axially displaced or otherwise manipulated by controlling the opposite end of the tissue pick.

47 Claims, 4 Drawing Sheets

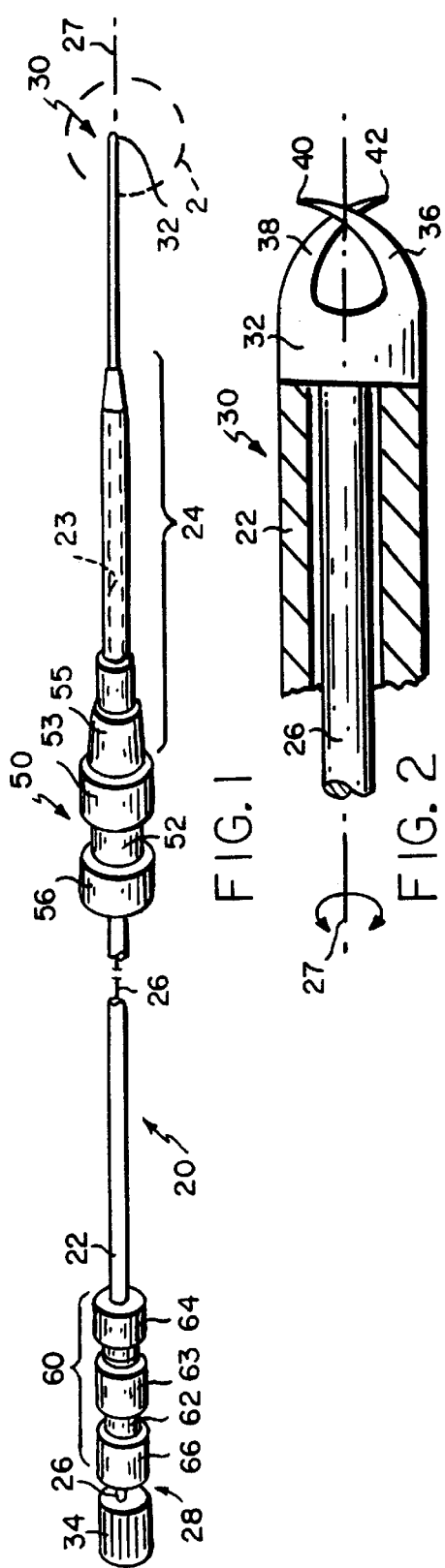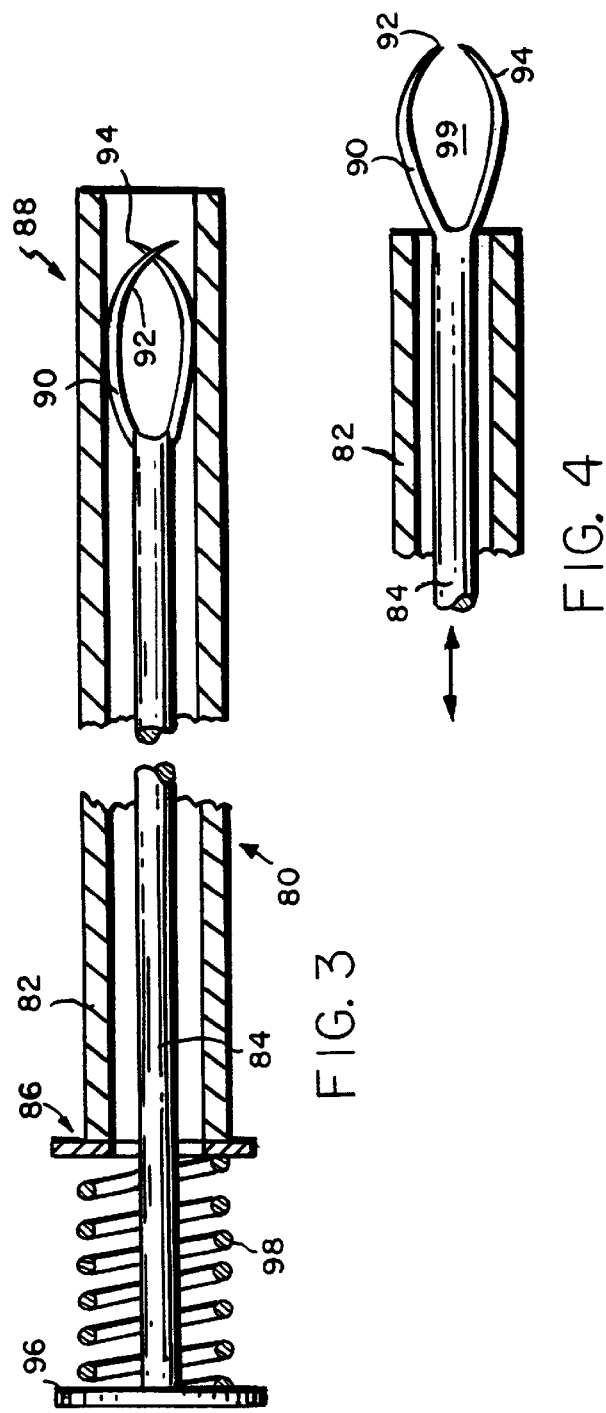

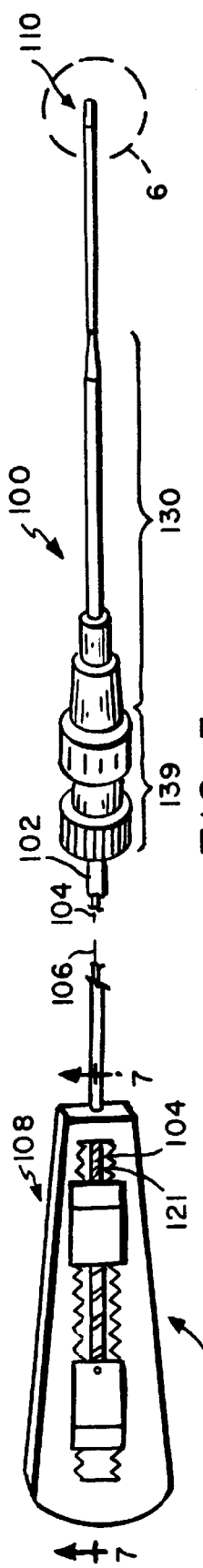
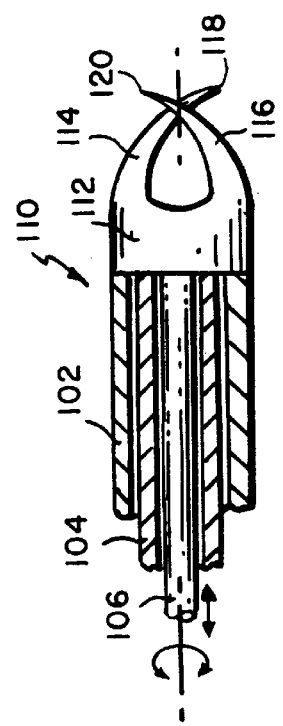
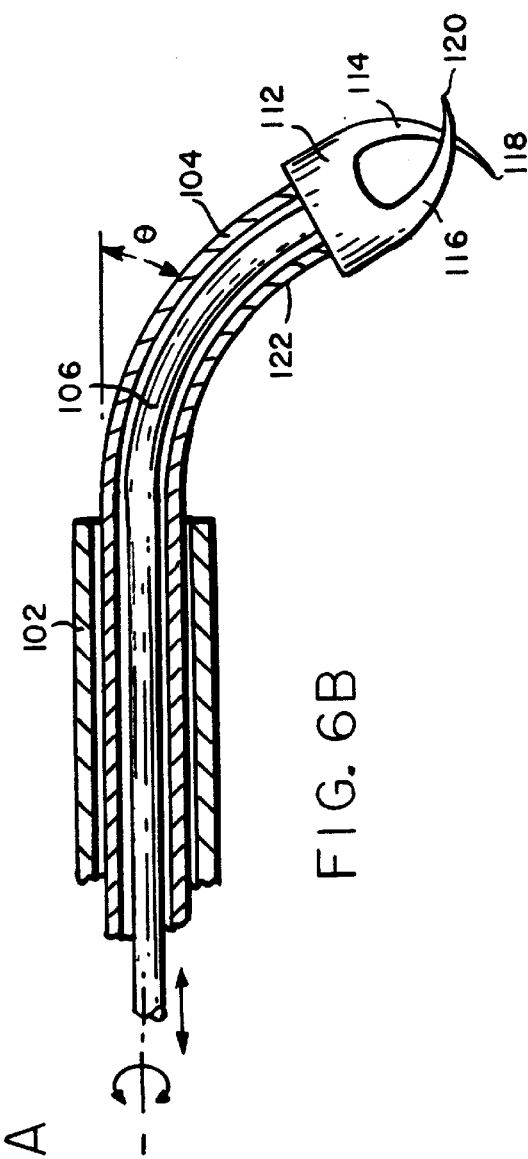
FIG. 5
FIG. 6A
FIG. 6B

TISSUE PICK AND METHOD FOR USE IN MINIMALLY INVASIVE SURGICAL PROCEDURES

BACKGROUND OF THE INVENTION

1. Field of the Invention

This invention relates generally to medical devices for use during surgery and, more particularly, to tissue picks for use in endoscopic, laparoscopic, or other minimally invasive surgeries.

2. Related Art

Tissue picks are commonly used by surgeons, for example, to lift tissue such as peritoneum, pleura, endocardium, organ capsules, skin, or any other tissue, hereafter referred to as target tissue, during invasive surgical procedures. Tissue picks are also commonly used when separating fine target tissue from an underlying area such as an artery which is not to be cut.

A conventional tissue pick is formed of a rigid material in the shape of a relatively short rod-like device having a handle end attached to a tissue grasping end. The tissue grasping end includes a double-pronged tip. To use a conventional tissue pick, during surgery, a surgeon orients and manipulates the tissue pick such that the double-pronged tip grasps the target tissue. The surgeon then moves the tissue pick, together with the target tissue, to a desired location. A second surgeon or other medical assistant then manually holds the tissue pick in the desired location while the surgical procedure is performed.

With the advent of less invasive surgeries, such as laparoscopic, thoracoscopic or endoscopic surgeries, the use of conventional tissue picks is limited primarily due to the relatively short length and rigidity of the instrument. However, the need to lift or move a target tissue during minimally invasive surgery remains. Generally, in such invasive surgeries, the body cavity area where the surgery is to occur is generally filled with a gas, typically carbon dioxide, to inflate the cavity to about six inches or so, thereby separating the outer tissue layers from the surgical field. A plurality of laparoscopic trocars are inserted through the outer tissue layers so as to extend into the inflated body cavity. One trocar may be used to receive a small fiber optic video camera or other video device. Other trocars may receive the surgical instruments required to perform the intended surgery.

Tedious surgical procedures have been developed to move the target tissue during minimally invasive laparoscopic surgery. Common to such procedures is the creation of a small incision at a location remote from the laparoscopic trocar. This small incision must extend through the many layers of outer tissue before reaching the inflated body cavity. A surgical needle and suture is then manipulated through the small incision into the body cavity. With a pair of graspers through the same or another incision, the needle is grasped and pushed through the target tissue. The needle is then released and subsequently grasped on the other side of the target tissue with the graspers and pulled back out through the incision. The suture is then anchored in some well-known manner, and the target tissue is retracted or moved into position. Alternatively, a separate trocar can be placed for a grasper or other instrument.

The inventors of the present invention have recognized certain disadvantages with the above approaches. For example, the area of the body where the relatively large incision is made for insertion of either the tissue pick or needle and suture is traumatized. Also, because the needle and suture pierce through the target tissue, it too is traumatized. After the surgery is complete, each layer of tissue through which the incision was made must be sutured and, therefore, is further traumatized. In addition, the method described above with sutures can be time consuming and tedious.

Another disadvantage arises during use of a conventional tissue pick in minimally-invasive surgeries. For example, in order to effectively grasp the target tissue, the tissue pick must be substantially orthogonal to the surface of the target tissue so that the tissue grasping end of the tissue pick can embed into the target tissue. This is sometimes difficult if not impossible to achieve, given the restricted surgical field.

SUMMARY OF THE INVENTION

The present invention is a minimally invasive tissue pick and associated methodology for manipulating tissue during minimally invasive procedures that overcomes the above and other disadvantages of conventional techniques. The present invention includes a tissue pick adapted for passage through a lumen that is inserted through the body of a patient undergoing a minimally invasive surgical procedure. A proximal end of the tissue pick, which extends outside the patient's body, may be manipulated by the surgeon so as to effect actuation of the tissue grasping device at a distal end of the tissue pick within the patient's body. Once manipulated so as to grasp the target tissue, the tissue grasping device remains attached to the target tissue, enabling the surgeon to move the tissue into a desired position.

The tissue pick may be configured to articulate the tissue grasping device relative to the tissue pick so as to position the tissue grasping device at an angle relative to the surface of the target tissue, thus facilitating grasping of the target tissue. This substantially eliminates the need to relocate the lumen and, subsequently, the tissue pick. The tissue pick may also include at least one locking mechanism to secure the tissue pick in a desired orientation. This frees the surgeon to more readily perform the intended surgical procedure.

In one aspect of the present invention, a tissue pick is disclosed. The tissue pick includes an elongated member having a proximal end and a distal end. The distal end is adapted to be inserted through a lumen. A tissue grasping member disposed at the distal end of the elongated member is adapted to be manipulated by controlling the proximal end of the elongated member to automatically grasp the tissue. Thus, an advantage of the present invention is that a less traumatic procedure for moving target tissue is provided, which may result in reduced risk of infection.

In another aspect, the tissue pick includes an outer tube adapted to be inserted through the lumen. The elongated member is disposed within the outer tube. In one embodiment, the elongated member defines a longitudinal axis and the tissue grasping member is rotatable about the longitudinal axis relative to the outer tube. In another aspect, the tissue pick includes a lock for locking the rotation of the grasping member, thereby reducing the need for additional surgical hands or additional surgical instruments. In still another aspect, the tissue pick includes a knob attached to the proximal end of the elongated member for facilitating rotation of the grasping member. In yet another aspect, the tissue pick includes a lock for locking longitudinal displacement of the tissue pick relative to the lumen, thereby further reducing the need for additional surgical hands or additional surgical instruments.

In still another aspect, the tissue pick includes a helix for imparting rotation of the tissue grasping member. The helix is formed on either the elongated member or the tissue grasping member. A cam follower cooperates with the helix and is adapted for linear movement relative to the helix. In one embodiment of the invention, the helix and the cam follower are disposed adjacent to the proximal end. In another embodiment, the helix and the cam follower are disposed adjacent to the distal end.

In yet another embodiment, the tissue grasping member includes at least two helically formed opposing prongs. The prongs grasp an outer portion of tissue upon rotation of the grasping member. In still another embodiment, the tissue grasping member includes at least two spring loaded arc-shaped opposing prongs cooperating with a housing. The tissue grasping member is adapted to be positioned in an extended position, wherein the prongs are disposed in an unbiased opened position substantially outside of the housing, and in a retracted position, wherein the prongs are disposed in a biased closed position substantially inside of the housing.

In an alternative embodiment, the elongated member articulates at an angle relative to the outer tube. In another aspect, the tissue pick includes a shape-memory inner tube disposed between the outer tube and the elongated member. In this embodiment, the inner tube has an extended position and a retracted position relative to the outer tube. The inner tube cooperates with the outer tube such that, when the inner tube is in the extended position, the inner tube, together with the elongated member, articulates at an angle relative to the outer tube and when the inner tube is in the retracted position, the inner tube, together with the elongated member is substantially coaxial with the outer tube. Thus, the location at which the tissue pick is inserted need not be precisely located relative to the target tissue.

In another aspect of the present invention, a tissue pick for use with a lumen is disclosed. The tissue pick defines a longitudinal axis and includes an outer tube adapted to be inserted through the lumen. Thus, an advantage of the present invention is that a less traumatic procedure for moving target tissue is provided resulting in reduced risk of infection. An axial lock is positioned between the outer tube and the lumen for locking longitudinal displacement of the outer tube relative to the lumen, thereby reducing the need for additional surgical hands or additional surgical instruments. An elongated member, having a distal end and a proximal end, is disposed within the outer tube. A tissue grasping member is disposed at the distal end of the elongated member. The tissue grasping member includes at least two helically formed opposing prongs for grasping target tissue. A knob is attached to the proximal end of the elongated member. The tissue grasping member is rotatable about the longitudinal axis relative to the outer tube by rotation of the knob, thereby causing the prongs to grasp the target tissue. A rotational lock is positioned between the outer tube and the elongated member for locking the rotation of the elongated member relative to the outer tube, thereby further reducing the need for additional surgical hands or additional surgical instruments.

In still another aspect of the present invention, a tissue pick for use with a lumen is disclosed. The tissue pick defines a longitudinal axis and includes a handle and an outer tube attached to the handle. The tissue pick is adapted to be inserted through the lumen. Thus, an advantage of the present invention is that a less traumatic procedure for moving target tissue is provided resulting in reduced risk of infection. An axial lock is positioned between the outer tube and the lumen for locking longitudinal displacement of the outer tube relative to the lumen, thereby reducing the need for additional surgical hands or additional surgical instruments. An elongated member is disposed within the outer tube. The elongated member has a distal end and a proximal end. The proximal end extends into the handle and a tissue grasping member is disposed at the distal end of the elongated member. The tissue grasping member includes at least two helically formed opposing prongs for grasping target tissue. A helix and a cam follower cooperate with the elongated member. The cam follower cooperates with the helix such that, when the cam follower moves linearly relative to the helix, the elongated member rotates about a longitudinal axis, thereby causing the prongs to grasp the target tissue. This tissue pick further includes a rotational lock positioned between the cam follower and the handle for locking the rotation of the elongated member relative to the outer tube, thereby further reducing the need for additional surgical hands or additional surgical instruments.

In yet another aspect of the present invention, a method of manipulating target tissue during surgery of a patient using a tissue pick is disclosed. The tissue pick defines a longitudinal axis and has an outer tube adapted to be inserted through a lumen. An elongated member, having a distal end and a proximal end, is disposed within the outer tube. A tissue grasping member is disposed at the distal end of the elongated member. The method includes the steps of inserting the tissue pick into a lumen, advancing the tissue pick toward the target tissue, and contacting the tissue with the tissue grasping member. The method further includes the steps of grasping the target tissue and retracting the tissue pick relative to the lumen to a desired position. Thus, an advantage of the present invention is that a less traumatic procedure for moving target tissue may be provided resulting in reduced risk of infection. In another aspect of the invention, a plurality of tissue picks may be inserted through a plurality of lumens, respectively.

In one embodiment, the tissue grasping member is rotatable about a longitudinal axis relative to the outer tube. The step of grasping the target tissue includes the step of rotating the elongated member. In another aspect, the method includes the step of locking the rotation of the elongated member relative to the outer tube, thereby reducing the need for additional surgical hands or additional surgical instruments.

In yet another aspect, the method includes the step of locking axial displacement of the tissue pick relative to the lumen, thereby further reducing the need for additional surgical hands or additional surgical instruments.

In still another aspect, the method includes the step of articulating the elongated member at an angle relative to the outer tube. In another embodiment, the articulating step includes the step of linearly advancing the elongated member relative to the outer tube. Thus, the location at which the tissue pick is inserted need not be precisely located relative to the target tissue.

In still another aspect of the present invention, a tissue pick is disclosed. The tissue pick defines a longitudinal axis and includes a tissue grasping member adapted to articulate at an angle relative to the longitudinal axis. Thus, an advantage of the present invention is that a less traumatic procedure for moving target tissue is provided resulting in reduced risk of infection. Further, the location at which the tissue pick is inserted need not be precisely located relative to the target tissue.

In one embodiment, the tissue grasping member is adapted to be positioned in a first position disposed substantially coaxial with the longitudinal axis and at least one second position disposed at an angle relative to the longitudinal axis.

In another embodiment, the tissue grasping member is adapted to articulate through a plurality of angles relative to the longitudinal axis.

In still another aspect of the invention, a minimally invasive surgical instrument is disclosed. The instrument includes an elongate member adapted for insertion through a lumen; and, a lock for locking the member in a desired orientation. In one embodiment, the lock locks the member in a desired axial position relative to the lumen. In another embodiment the lock locks the ember in a desired rotational position relative to the lumen.

In yet another aspect of the invention, a surgical instrument is disclosed. The instrument includes an elongated member adapted for insertion through a lumen; a working end disposed at one end of said member; and a remote end disposed at another end of the member and coupled to the working end. The remote end is adapted for rotation such that rotation of the remote end causes the working end to rotate.

In still another aspect of the invention, a surgical instrument is disclosed. The instrument includes an outer tube adapted to be inserted through a lumen; and, a shape memory inner member disposed within the outer tube. The inner member is adapted for linear movement relative to the outer tube into an extended position and a retracted position. The inner member cooperates with the outer tube such that, when the inner member is in the extended position, the inner member articulates at an angle relative to the outer tube. When the inner member is in the retracted position, the inner member is substantially coaxial with the outer tube.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of less trauma induced on the patient.

Further features and advantages of the present invention as well as the structure and operation of various embodiments of the present invention are described in detail below with reference to the accompanying drawings.

BRIEF DESCRIPTION OF THE DRAWINGS

The invention will now be described, by way of example, with reference to the accompanying drawings, in which:

FIG. 1 is a perspective view of a tissue pick according to one embodiment of the present invention;

FIG. 2 is an enlarged view of the area encircled by line 2 of FIG. 1;

FIGS. 3 and 4 show an alternative embodiment of the tissue pick;

FIG. 5 is a perspective view of an alternative embodiment of the tissue pick of to the present invention;

FIG. 6a is an enlarged view of the area encircled by line 6 of FIG. 5 showing the end of the tissue pick in a first orientation;

FIG. 6b is an enlarged view of the area encircled by line 6 of FIG. 5 showing the end of the tissue pick in a second orientation;

DETAILED DESCRIPTION

Figure 7:
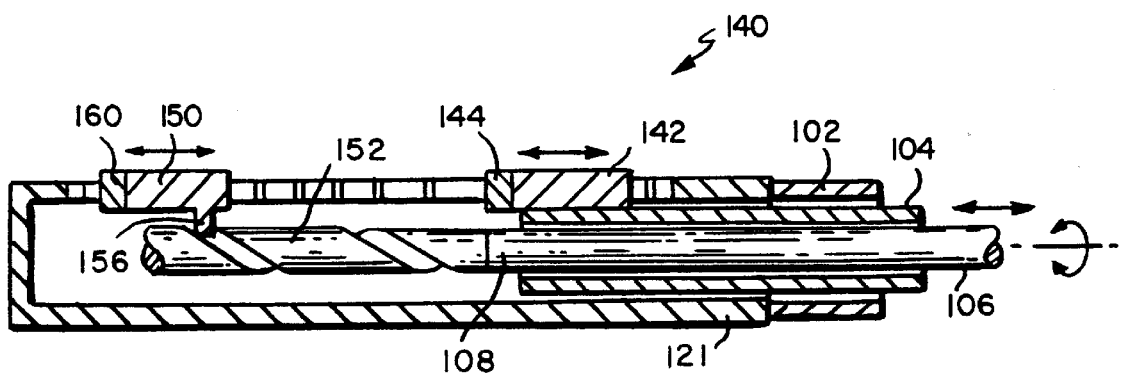
FIG. 7 is a cross-sectional view of a portion of the tissue pick taken along line 7—7 of FIG. 5.

A tissue pick of the present invention is adapted for passage through a lumen formed in, for example, a trocar or catheter. This enables the tissue pick to be advantageously used in, for example, minimally invasive surgeries, such as endoscopic, laparoscopic or thoracoscopic surgery, to lift a target tissue. The target tissue may be, for example, peritoneum, pleura, endocardium, organ capsules, skin or any other tissue. The trocar, catheter, or other device through which the lumen extends is inserted into the body of a patient undergoing a surgical procedure and the tissue pick is inserted into the lumen. A tissue grasping device at a distal end of the tissue pick is manipulated to be positioned adjacent the target tissue to grasp and move the tissue into a desired position so that a surgeon may more readily perform the intended surgical procedure. The tissue grasping end of the tissue pick may be adapted to articulate at an angle by controlling the opposite end such that the tissue grasping end becomes substantially orthogonal to the surface of the target tissue to facilitate grasping the target tissue.

It is to be appreciated that the lumen, may be any channel or passageway in any small tube-like device including an angiocatheter or other catheter, an endoscope, a laparoscope, a trocar or any other tube-like device now or later developed that is inserted into a body cavity to keep a port open so as to pass surgical instruments therethrough. For convenience, the tissue pick of the present invention will be described with reference to a catheter. However, it is to be appreciated that the tissue pick of the present invention may be used independently or with any of the aforementioned devices.

FIG. 1 is a perspective view of one embodiment of a tissue pick configured for use in a catheter. FIG. 2 is an enlarged view of the region encircled by line 2 of FIG. 1. Tissue pick 20 includes an elongated outer tube 22, preferably about 12–18 inches long, adapted to be insertable into a working channel, or lumen 23, of a catheter 24. An elongated, semi-rigid shaft 26, defining a longitudinal axis 27, is received within tube 22. The shaft 26 includes a proximal end or remote end 28 and a distal end or working end 30. The distal end 30 includes a tissue grasping member 32 for grasping a target tissue (not shown). In the illustrative example shown in FIG. 2, the tissue grasping member 32 includes two nearly horizontally opposing prongs 36, 38, which are each helically formed, having tips 40 and 42, respectively. The proximal end 28 of shaft 26 may be connected to a knob 34 or other device for manipulating the shaft 26 and the tissue grasping member 32, as will become apparent.

Tissue pick 20 may include an axial lock 50 that locks the outer tube 22 relative to the catheter 24 to prevent relative axial movement therebetween. In one embodiment, axial lock 50 includes a housing 52 having a standard Luer connector 53 for securing the axial lock 50 to the proximal end 55 of catheter 24. The axial lock 50 further includes a glandular member (not shown) disposed between the housing 52 and the outer tube 22. A cap 56, when screwed onto the housing 52, compresses the glandular member in a tight sealing engagement relative to the outer tube 22 to reduce any axial movement therebetween. This tight sealing engagement is also effective in reducing the possibility of leakage of fluids or the injected gas from the body cavity. Such a locking device is typically termed a Touhy-Borst, which may be purchased from the Becton-Dickinson Corporation, Franklin Lakes, N.J., U.S.A. It is to be appreciated that other suitable locks which axially lock the outer tube 22 relative to the catheter 24 may be used.

The tissue pick 20 may also include a rotational lock 60 constructed and arranged to rotationally lock outer tube 22 and the shaft 26. In this illustrative example, rotational lock 60 is of a similar construction to axial lock 50. It should be understood, however, that rotational lock 60 may be any suitable locking device or arrangement adapted for rotationally locking two concentric members. Accordingly, the rotational lock 60 includes a housing 62 having a standard Luer connector 63 formed within housing 62. A plug 64 is secured to outer tube 22 and is adapted for insertion into the Luer connector 63 for securing the outer tube 22 to the housing 62. The rotational lock 60 further includes a glandular member (not shown) formed within the housing 62. The shaft 26 passes through the glandular member and is attached to the knob 24. A cap 66, having an opening to allow the shaft 26 to pass therethrough, is also provided. When cap 66 is screwed onto the housing 62, the glandular member is compressed in a tight sealing engagement relative to the shaft 26 to reduce the rotational movement thereof, as well as to reduce the possibility of leakage of fluids or gas.

During a surgical procedure, catheter 24 is inserted into a body cavity of a patient. The tissue pick 20 is then inserted into the catheter 24 and positioned such that the distal end 30 having the tissue grasping member 32 touches the target tissue. Next, the knob 34, together with the shaft 26, is rotated, for example, in a counter-clockwise manner, such that the nearly horizontally opposing tips 40, embed into the outer fine membrane of the target tissue. The rotational lock 60 is then locked such that any additional rotation of the shaft 26 relative to the outer tube 22 is reduced. This, in return, reduces any inadvertent increased trauma to the target tissue caused by a further rotation or any inadvertent releasing of the target tissue. The surgeon may then axially withdraw or retract the tissue pick 20 relative to the catheter 24 to a desired position in which the target tissue is moved away from the surgical field. Once the desired axial displacement is achieved, the axial lock 50 is locked to reduce any further axial movement of the tissue pick 20 relative to the catheter 24 and to reduce any leakage therebetween. The surgeon's hands are now free to complete the surgical procedure without having to hold the tissue pick 20. To release the target tissue, the shaft 26 is rotated in an opposite direction, for example, clockwise, whereby the prongs 36, 38 of the tissue grasping member 32 release from the target tissue.

The outer tube 22 has an outer diameter sized to accommodate the catheter and an inner diameter sized to accommodate the shaft 26. In a preferred embodiment, the outer tube 22 has an outside diameter approximately equal to that of a typical catheter needle (for example, 17 gage or 0.058 in.) and has a wall thickness of about 5–10 mills, although a thicker or thinner wall may be suitable. Also, although the shaft 26 is shown and described as a semi-rigid cylindrically-shaped shaft, the shaft may be formed of a cable or a tube of any cross-sectional shape, and may be stiff or flexible and may be made of any suitable material, including, for example, stainless steel or plastic. The tissue grasping member 32 may be connected to the shaft by any suitable means such as crimping or brazing.

In some instances, it may be desirable to manipulate the tissue grasping member without having to rotate any portion of the tissue pick. FIGS. 3 and 4 show an alternative embodiment of a tissue pick incorporating such a feature. Tissue pick 80 includes an outer tube 82 adapted to be inserted into a working channel of a catheter (not shown in this embodiment) and a semi-rigid shaft 84 received within the outer tube 82. The shaft 84 includes a proximal end 86 and a distal end 88 with a tissue grasping member 90 disposed at the distal end 88. The tissue grasping member 90 includes two opposing arcuately shaped prongs 92, 94 formed of a shape memory material biased in an open position (see FIG. 4). Such a material may be spring steel, Nickel-Titanium, stainless steel or plastic. A plunger 96 is formed at the proximal end 86 and a spring 98 may be provided to bias the shaft 84 away from the outer tube 82 such that the tissue grasping member 90 is in a closed position and is completely housed within the outer tube 82.

As discussed with reference to the embodiments of FIGS. 1 and 2, the outer tube 82 of the embodiment of FIGS. 3 and 4 has an outer diameter sized to accommodate the catheter and in inner diameter sized to accommodate the shaft 84. In a preferred embodiment, the outer tube 82 has a wall thickness of about 5-10 mills, although a thicker or thinner wall may be suitable. Also, although the shaft 82 is shown and described as a semi-rigid cylindrically shaped shaft, the shaft may be formed of a cable or a tube of any cross-sectional shape, and may be stiff or flexible and may be made of stainless steel or plastic.

To use this embodiment of the tissue pick 80, a catheter (not shown) is placed into a patient. The tissue pick 80 is then inserted into the catheter with the tissue grasping member 90 biased in its retracted position via spring 98, as shown in FIG. 3. The tissue grasping member 90 is brought into proximity to the target tissue without actually contacting the target tissue. As the surgeon actuates the plunger 96, the shaft 84 moves in an axial direction such that the tissue grasping member 90 emerges from the outer tube 82, thereby causing the opposing prongs 92, 94, because of the shape-memory material, to expand into an open position, as shown in FIG. 4. The tissue pick 80 is then brought closer to the target tissue to allow the target tissue to move into the gap 99 between the two prongs 92, 94. Next, the surgeon releases the plunger 96 and, with the action of the spring 98, the shaft 84 moves within the outer tube 82 to collapse the prongs 92, 94, thereby capturing the target tissue within the gap 99 and simultaneously retracting it to a desired position. Of course, one or more locks may be used to limit any axial displacement or leakage.

The embodiments of FIGS. 1–4 optimally perform when the tissue pick is positioned substantially orthogonal to the surface of the target tissue because only one of the prongs may inefficiently grasp the target tissue. However, in some operating conditions placing the tissue pick in an orientation substantially orthogonal to the surface of the target tissue may not be possible, due to, for example, the location of the target tissue, the location of the lumen relative to the target tissue, or the experience of the user. Accordingly, the tissue pick of the present invention may be constructed and arranged such that the tissue grasping member may articulate through a plurality of angles relative to the longitudinal axis of the tissue pick, thereby positioning the tissue grasping member substantially orthogonal to the surface of the target tissue. One such embodiment is described below with reference to FIGS. 5–8.

FIG. 5 is a perspective view of this embodiment of a tissue pick configured to articulate. In this embodiment, tissue pick 100 includes an outer tube 102, an inner tube 104 disposed within the outer tube 102 adapted for axial movement therein, and a flexible shaft 106 disposed within the inner tube 104 for rotational movement therein. The shaft 106 includes a proximal end 108 and a distal end 110. A tissue grasping member 112 is attached to the shaft 106 at the distal end 110. In this illustrative example of tissue pick 100, tissue grasping member 112 is similar to that described above with respect to tissue pick 20. Tissue grasping member 112 includes two nearly horizontally opposing prongs 114, 166, which are helically formed, such that when the tissue grasping member 112 is rotated, the tips 118, 120 of the prongs 116, 118, respectively, embed into the outer portion of the target tissue. The inner tube 104 has a proximal end 121 and a distal end 122.

In the embodiment described with reference to FIGS. 5–8, the inner tube 104 is formed of a shape-memory material. Such a material may be spring steel, Nickel-Titanium, plastic or any other material now or later developed that has the characteristic of significantly deflecting and returning to a desired rest position.

The shaft 106 is formed of a flexible material such as stainless steel, plastic or any other suitable material. The material chosen is sufficiently flexible to allow rotation of the shaft 106 about is axis when the shaft is in a bent configuration, as will be appreciated hereinafter.

When the inner tube 104 is retracted within the outer tube 102, the two remain substantially coaxial with each other (as shown in FIG. 6a, which represents an enlarged view of distal end 110 in a retracted position encircled by line 6 of FIG. 5). However, when the inner tube 104 is moved such that its distal end 122 emerges from the outer tube 102, the distal end 122 bends at an angle θ relative to the outer tube 102 (as shown in FIG. 6b, which represents an enlarged view of distal end 110 in an extended position encircled by line 6 of FIG. 5). The inner tube 104 bends because it is formed with a shape memory material with its rest position having a bend with a maximum angle θ. Once retracted into the outer tube 102, the inner tube 104 is in a biased position wherein the inner tube 104 is in the substantially coaxial alignment relative to the outer tube 102. Thus, the amount of angular deflection of the inner tube 104 relative to the outer tube 102 is determined by the amount of extension of the inner tube 104 relative to the outer tube 102. To change the angle θ, the inner tube 102 is positioned to a desired axial displacement relative to the outer tube 102. According to the present invention, the angle θ may range from about 0° to 180°, although a range from about 0° to 90° is preferable.

In use, the tissue pick 100 is inserted into a catheter 130 and is positioned such that the tissue grasping member 112 is in proximity to the target tissue. However, in contrast to the example of FIGS. 1 and 2, if the tissue grasping member 112 is not initially substantially orthogonal to the surface of the target tissue, the tissue pick is retracted slightly relative to the catheter and the inner tube 104 is axially displaced relative to the outer tube 102, such that the inner tube 104 articulates relative to the outer tube 102, until the tissue grasping member 112 becomes substantially orthogonal to and in contact with the surface of the target tissue. Once in this position, the shaft 106 is rotated such that the prongs 114, 116 of the tissue grasping member 112 embed into the outer fine membrane of the target tissue. Once embedded, the tissue pick 100 is retracted relative to the catheter 130, to lift the target tissue to a desired position.

Continuing with reference to FIG. 5, an axial lock 139 locks the outer tube 102 to the catheter 130 to prevent relative axial movement. Such an axial lock 139 is similar to axial lock 50 described with reference to FIG. 1. The tissue pick 100 may also include additional locks to lock the inner tube 104 relative to the outer tube 102 and to lock the shaft 106 relative to the outer tube 102, as will be fully described with reference to FIGS. 7 and 8.

In the embodiment described with reference to FIGS. 5–8, the outer tube 102 has an outer diameter sized to fit within the catheter and inner diameter sized to accommodate both the inner tube 104 and the shaft 106. In a preferred embodiment, the outer tube has an outer diameter of about 17 gage (0.058 in.) and a wall thickness of about 5–10 mills, although a larger or smaller diameter or a thicker or thinner wall may be suitable. Also, although the shaft 106 is shown and described as a flexible, cylindrically-shaped shaft, the shaft may be formed of a cable or a tube or any cross-sectional shape and may be made of stainless steel or plastic. The tissue grasping member 32 may be connected to the shaft by any suitable means such as crimping or brazing.

Although the embodiment described with reference to FIGS. 5–8 includes the helically formed prongs 114, 116, it is to be appreciated that the tissue grasping member 112 may be formed with the opposing spring-like prongs, as described with reference to FIGS. 3 and 4. In such an embodiment, although not shown, the shaft may be axially moveable relative to the inner tube to cause the tissue grasping member to open and receive the target tissue as well as to grasp and hold the target tissue into a desired position.

Referring now in particular to FIG. 7, one embodiment of a handle 140 of the tissue pick 100 of FIG. 5 is illustrated. Handle 140 is fixed to the outer tube 102 and a first sliding actuator 142 is fixed to the inner tube 104. The actuator 142 is housed within the handle 140 and is adapted to move axially relative thereto, thereby causing the inner tube 104 to move axially relative to the outer tube 102.

A second sliding actuator 150 may be provided in the handle 140 which translates linear motion of the actuator 150 to rotational motion of the shaft 106. This may be accomplished with a helix 152 formed on the proximal end 108 of the shaft 106, and a cam follower 156 formed on the actuator 150. Thus, as the actuator 150 slides relative to the handle 140, the cam follower 156 forces the shaft 106 to rotate. It is to be appreciated that the helix 152 may be integrally formed with the proximal end 108 or may be a separate member attached to the proximal end 108, as desired.

Again, an axial lock 160 may be formed on the actuator 150 to lock the actuator 150 relative to the handle 140 to reduce any translation relative therebetween, which would ultimately result in a rotation of the shaft 106.

Although the actuators 142, 150 are housed within a handle 140, as shown in the embodiments with respect to FIGS. 5–7, those skilled in the art will recognize in view of this disclosure that other actuating mechanisms may be used, including a multiple plunger arrangement as previously described or a nested actuator arrangement whereby the second sliding actuator 150 is housed within the first sliding actuator 142. This nesting arrangement may be desirable because, when attempting to move the inner tube without causing the shaft to rotate, both actuators must move in unison. Only when rotation of the shaft is desired is the second actuator moved independent of the first.

Figure 8:
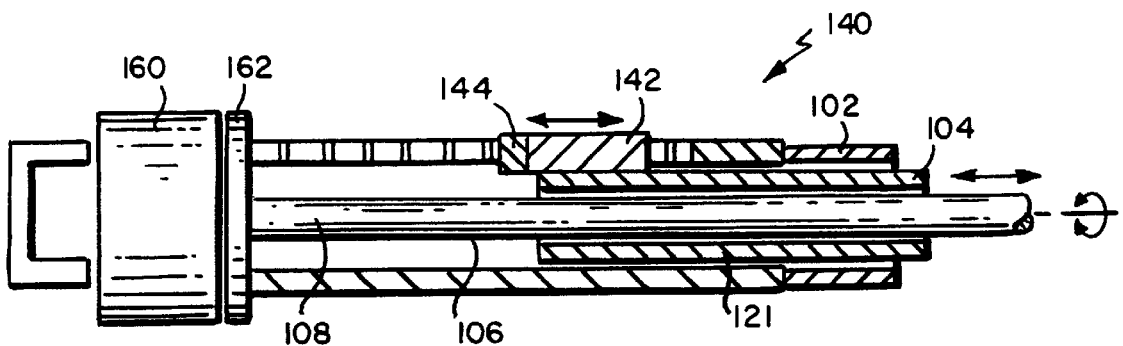
FIG. 8 is an alternative embodiment of the portion of the tissue pick shown in FIG. 7.

FIG. 8 illustrates another embodiment of the handle 140, wherein a knob 160 may be attached to the shaft 106 and housed within the handle 140 rather than provide the second sliding actuator 150. The shaft 106 may be rotated by rotating the knob 160 relative to the handle 140. A rotational lock 162 may be provided to lock the rotation of the shaft 106.

Figure 9:
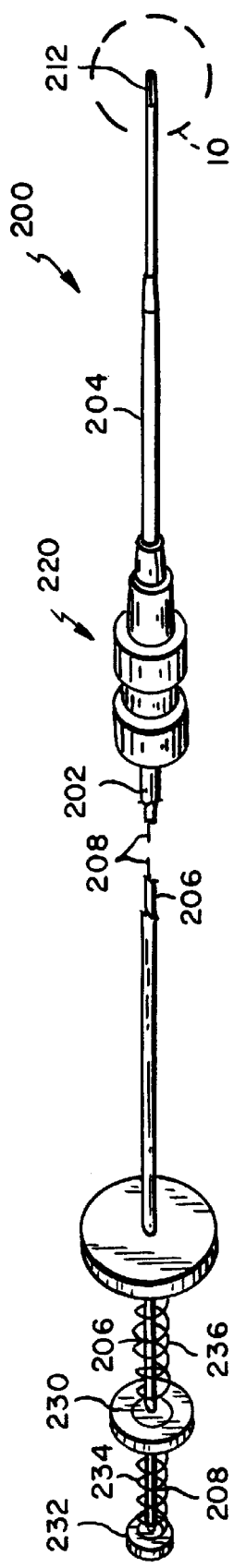
FIG. 9 is a perspective view of another alternative embodiment of the tissue pick of the present invention.
Figure 10:
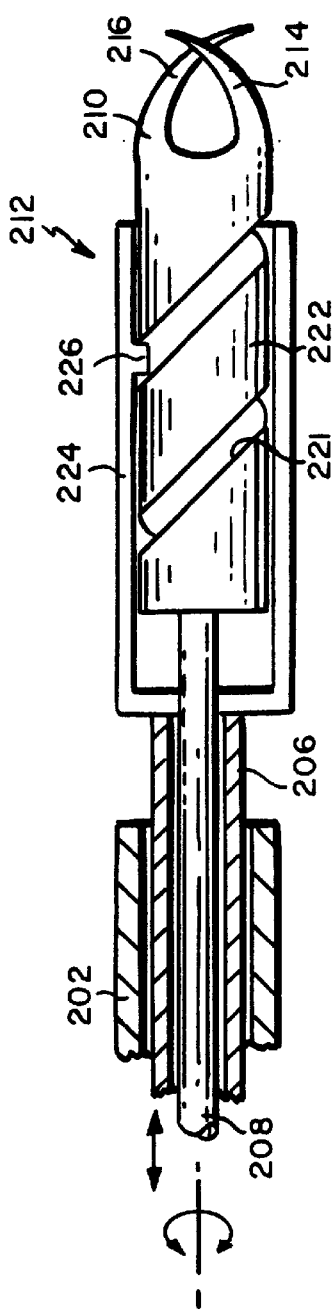
FIG. 10 is an enlarged view of the area encircled by line 10 of FIG. 9 showing the end of the tissue pick.

The embodiment described with reference to FIG. 7 shows the helix 152 which translates linear motion to rotational motion formed at the proximal end 108 of the shaft. However, as shown in the embodiment of FIGS. 9 and 10, the helix may be formed at the distal end of the tissue pick. In this illustrative example of FIG. 9, a tissue pick 200 is shown in perspective. Tissue pick 200 includes an outer tube 202 adapted to be inserted into a catheter 204, an inner tube 206 disposed within the outer tube 202 and a flexible shaft 208 disposed within the inner tube 202. An axial lock 220 may be used to axially lock the outer tube 202 relative to the catheter 204, as described with reference to FIGS. 1–8. As best shown in FIG. 10 which is an enlarged view of the area encircled by line 10 of FIG. 9, a tissue grasping member 210 is formed at the distal end 212 of the shaft 208. The tissue grasping member 210 includes helically formed prongs 214, 216, as described with reference to FIGS. 1, 2 and 5–8.

The tissue grasping member 210 is formed with a helix, such as a helical groove 221 in a body 222, which is received within a housing 224. The housing 224 is formed with a cam follower 226, which is adapted to engage the groove 221. The housing 224 is attached to the inner tube 206 if an articulating tissue pick is employed, as in this example. Thus, when the shaft 208 moves axially relative to the inner tube 206, the tissue grasping member 210 rotates relative to the housing 224, thereby causing the prongs 214, 216 of the tissue grasping member 210 to grasp the target tissue. Those skilled in the art will recognize in view of this disclosure that although the body of the tissue grasping member is formed with a helix and the cam follower is formed on the housing, the opposite may be true, wherein the housing may include a helix, which may be a groove or a raised portion, and the cam follower may be formed on the tissue grasping member.

As described above with reference to the embodiment of FIGS. 5–8, the inner tube 206 of the embodiment of FIGS. 9 and 10 is formed of a shape-memory material such as spring-steel, Nickel-Titanium, plastic or any other material now or later developed that has the characteristic of significantly deflecting and returning to a desired rest position. Also, the shaft 208 is formed of a flexible material such as stainless steel, plastic or any other suitable material. The material chosen is sufficiently flexible to allow rotation of the shaft 208 about its axis when the shaft is in a bent configuration.

Movement of the inner tube 206 and the shaft 208, in the example of FIGS. 9 and 10, is accomplished through a nesting plunger-type arrangement, wherein a first plunger 230 is attached to the inner tube 206 and a second plunger 232 is attached to the shaft 208. A first and second spring 234, 236 may be used to bias the axial position of the inner tube 206 and the rotational position of the shaft 208 to desired rest positions, respectively. In a preferred embodiment, the rotational rest position may be such that the tissue grasping member 210 is in a tissue grasping rotational orientation. Thus, when the plunger 232 is depressed, the tissue grasping member 210, may rotate in a direction opposite the direction of the prongs 214, 216 such that the target tissue cannot be grasped. Upon release of the plunger 232, the spring 234 will push the plunger 232 axially, thereby causing the tissue grasping member 210 to rotate into a position such that the prongs 214, 216 may grasp the target tissue.

As discussed with reference to the embodiment of FIGS. 5–8, the outer tube 202 of the embodiment of FIGS. 9 and 10 has an outer diameter sized to fit within the catheter and an inner diameter sized to accommodate both the inner tube 206 and the shaft 208. In a preferred embodiment, the outer tube has an outer diameter of about 17 gage (0.058 in.) and has a wall thickness of about 5–10 mills, although a larger or smaller diameter or a thick or thinner wall may be suitable. Also, although the shaft 208 is shown and described as a flexible cylindrically-shaped shaft, the shaft may be formed of a cable or tube of any cross-sectional shape and may be made of stainless steel or plastic. The tissue grasping member 32 may be connected to the shaft by any suitable means such as crimping or brazing.

According to another aspect of the invention, it may be advantageous to use a plurality of tissue picks of the present invention during a surgical procedure so as to stabilize a tissue structure for reconstruction, for example. In addition, a plurality (four, for example) may be used to stabilize the heart during a "beating heart" procedure. Other applications of a single or multiple tissue picks according to the present invention will be readily apparent to those skilled in the art.

In addition, as should be apparent to those skilled in the art in view of this disclosure, any of the disclosed devices, as well as any other suitable device, used to actuate the inner tube or the shaft, may be used in any of the embodiments. Also, although the helix shown in the examples described herein used to translate linear motion to rotational motion is in the form of a groove or a raised portion, a spring may be used as the helix. Thus, as used herein, the term helix means any helically shaped form or helical member used to transform linear motion to rotational motion.

While the best mode for carrying out the invention has been described in detail, those skilled in the art to which this invention relates will recognize various alternative embodiments including those mentioned above as defined by the following claims.

What is claimed is:

1. A tissue pick comprising:
   an elongated member adapted to be inserted through a lumen, said elongated member having a distal end and a proximal end; and,
   a tissue grasping member disposed at said distal end of said elongated member, with said tissue grasping member being adapted to be manipulated by controlling said proximal end of said elongated member, wherein said tissue grasping member comprises at least two helically formed opposing prongs, with said prongs grasping an outer portion of tissue upon rotation of said grasping member.

2. The tissue pick according to claim 1 further comprising:
   an outer tube adapted to be inserted into the lumen, with said elongated member being disposed within said outer tube.

3. The tissue pick according to claim 2 wherein said elongated member defines a longitudinal axis, and wherein said tissue grasping member is rotatable about said longitudinal axis relative to said outer tube.

4. The tissue pick according to claim 3 further comprising:
   a lock for locking the rotation of said grasping member.

5. The tissue pick according to claim 3 further comprising:
   a knob attached to said proximal end of said elongated member for facilitating rotation of said grasping member.

6. The tissue pick according to claim 3 further comprising:
   a helix for imparting rotation of said grasping member, with said helix being formed on one of said elongated member and said grasping member and a claim follower cooperating with said helix and adapted for linear movement relative to said helix.

7. The tissue pick according to claim 6 wherein said helix and said cam follower are disposed adjacent said proximal end.

8. The tissue pick according to claim 6 wherein said helix and said cam follower are disposed adjacent said distal end.

9. The tissue pick according to claim 1 further comprising:

a lock for locking longitudinal displacement of said tissue pick relative to the lumen.

10. The tissue pick according to claim 1 wherein said tissue grasping member comprises at least two spring loaded arc-shaped opposing prongs cooperating with a housing, said tissue grasping member being adapted to be positioned in an extended position, wherein said prongs are disposed in an unbiased opened position substantially outside of said housing, and in a retracted position, wherein said prongs are disposed in a biased closed position substantially inside of said housing.

11. The tissue pick according to claim 1 wherein said elongated member articulates at an angle relative to said outer tube.

12. The tissue pick according to claim 11 further comprising:

a shape-memory inner tube disposed between said outer tube and said elongated member.

13. The tissue pick according to claim 12 wherein said inner tube has an extended position and a retracted position relative to said outer tube, with said inner tube cooperating with said outer tube such that, when said inner tube is in said extended position, said inner tube, together with said elongated member, articulates at an angle relative to said outer tube and when said inner tube is in said retracted position, said inner tube, together with said elongated member is substantially coaxial with said outer tube.

14. A tissue pick defining a longitudinal axis and comprising:

an outer tube adapted to be inserted through a lumen;

an axial lock positioned between said outer tube and the lumen for locking longitudinal displacement of said outer tube relative to the lumen;

an elongated member disposed within said outer tube, said elongated member having a distal end and a proximal end;

a tissue grasping member disposed at said distal end of said elongated member, said tissue grasping member comprising at least two helically formed opposing prongs for grasping target tissue;

a knob attached to said proximal end of said elongated member, said tissue grasping member being rotatable about said longitudinal axis relative to said outer tube by rotation of said knob, thereby causing said prongs to grasp the target tissue; and, a rotational lock positioned between said outer tube and said elongated member for locking the rotation of said elongated member relative to the outer tube.

15. A tissue pick defining a longitudinal axis and comprising:

a handle;

an outer tube attached to said handle and adapted to be inserted through a lumen;

an axial lock positioned between said outer tube and the lumen for locking longitudinal displacement of said outer tube relative to the lumen;

an elongated member disposed within said outer tube, said elongated member having a distal end and a proximal end, with said proximal end extending into said handle;

a tissue grasping member disposed at said distal end of said elongated member, said tissue grasping member comprising at least two helically formed opposing prongs for grasping target tissue;

a helix and a cam follower cooperating with said elongated member, said cam follower cooperating with said helix such that, when said cam follower moves linearly relative to said helix, said elongated member rotates about a longitudinal axis, thereby causing said prongs to grasp the target tissue; and, a rotational lock positioned between said cam follower and said handle for locking the rotation of said elongated member relative to the outer tube.

16. The tissue pick according to claim 15 further comprising:

a shape-memory inner tube having a proximal end extending into said handle and being disposed between said outer tube and said elongated member, wherein said inner tube is adapted for linear movement and is adapted to move to an extended position and to a retracted position relative to said outer tube, said inner tube cooperating with said outer tube such that, when said inner tube is in said extended position, said inner tube, together with said elongated member, articulates at an angle relative to said outer tube and when said inner tube is in said retracted position, said inner tube, together with said elongated member is substantially coaxial with said outer tube.

17. The tissue pick according to claim 16 further comprising:

an actuator disposed within said handle and attached to said inner tube for facilitating linear movement of said inner tube.

18. A method of manipulating target tissue during surgery of a patient using a tissue pick, the tissue pick defining a longitudinal axis and having an outer tube adapted to be inserted through a lumen, an elongated member disposed within the outer tube, the elongated member having a distal end and a proximal end, and a tissue grasping member disposed at the distal end of the elongated member, said method comprising the steps of:

inserting the tissue pick through a lumen;

advancing the tissue pick toward the target tissue;

contacting the tissue with the tissue grasping member;

rotating the elongated member to grasp the target tissue;

retracting the tissue pick relative to the lumen to a desired position; and locking the rotation of the elongated member relative to the outer tube.

19. The method according to claim 18 further comprising the step of:

locking axial displacement of the tissue pick relative to the lumen.

20. The method according to claim 18 further comprising the step of:

articulating the elongated member at an angle relative to the outer tube.

21. The method according to claim 20 wherein said articulating step comprises the step of:

linearly advancing the elongated member relative to the outer tube.

22. A tissue pick, defining a longitudinal axis, comprising:
a tissue grasping member adapted to articulate at an angle relative to the longitudinal axis;
an outer tube; and
an elongated member disposed within said outer tube and having a distal end, said tissue grasping member being disposed at said distal end of said elongated member, and a shape-memory inner tube disposed between said outer tube and said elongated member, wherein said inner tube is adapted to be positioned in an extended Position and in a retracted position relative to said outer tube, said inner tube cooperating with said outer tube such that, when said inner tube is in said extended position, said inner tube, together with said elongated member, articulates an angle relative to said outer tube and when said inner tube is in said retracted position, said inner tube, together with said elongated member, is substantially coaxial with said outer tube.

23. The tissue pick according to claim 22 wherein said tissue grasping member is adapted to be positioned in a first position disposed substantially coaxial with the longitudinal axis and at least one second position disposed at an angle relative to the longitudinal axis.

24. The tissue pick according to claim 22 wherein said tissue grasping member is adapted to articulate through a plurality of angles relative to the longitudinal axis.

25. The tissue pick according to claim 22 wherein said tissue grasping member is rotatable about the longitudinal axis.

26. A tissue pick comprising:
an elongated member disposed within an outer tube and adapted to be inserted through a lumen, said elongated member having a distal end and a proximal end, and articulates at an angle relative to said outer tube;
a shape-memory inner tube disposed between said outer tube and said elongated member; and
a tissue grasping member disposed at said distal end of said elongated member, with said tissue grasping member being adapted to be manipulated by controlling said proximal end of said elongated member.

27. The tissue pick according to claim 26, wherein said elongated member defines a longitudinal axis, and wherein said tissue grasping member is rotatable about said longitudinal axis relative to said outer tube.

28. The tissue pick according to claim 27 comprising:
a lock for locking the rotation of said grasping member.

29. The tissue pick according to claim 27 comprising:
a knob attached to said proximal end of said elongated member for facilitating rotation of said grasping member.

30. The tissue pick according to claim 27 further comprising:
a helix for imparting rotation of said grasping member, with said helix being formed on one of said elongated member and said grasping member and a cam follower cooperating with said helix and adapted for linear movement relative to said helix.

31. The tissue pick according to claim 30, wherein said helix and said cam follower are disposed adjacent said proximal end.

32. The tissue pick according to claim 30, wherein said helix and said cam follower are disposed adjacent said distal end.

33. The tissue pick according to claim 26 comprising:
a lock for locking longitudinal displacement of said tissue pick relative to the lumen.

34. The tissue pick according to claim 26, wherein said tissue grasping member comprises at least two helically formed opposing prongs, with said prongs grasping an outer portion of tissue upon rotation of said grasping member.

35. The tissue pick according to claim 26, wherein said tissue grasping member comprises at least two spring loaded arc-shaped opposing prongs cooperating with a housing, said tissue grasping member being adapted to be positioned in an extended position, wherein said prongs are disposed in an unbiased opened position substantially outside of said housing, and in a retracted position, wherein said prongs are disposed in a biased closed position substantially inside of said housing.

36. A tissue pick comprising:
an elongated member adapted to be inserted through a lumen, said elongated member having a distal end and a proximal end defining a longitudinal axis;
an outer tube adapted to be inserted into the lumen, with said elongated member being disposed within said outer tube;
a tissue grasping member disposed at said distal end of said elongated member, with said tissue grasping member being adapted to be manipulated by controlling said proximal end of said elongated member, and wherein said tissue grasping member is rotatable about said longitudinal axis relative to said outer tube; and
a helix for imparting rotation of said grasping member, with said helix being formed on one of said elongated member and said grasping member.

37. The tissue pick according to claim 36 comprising a lock for locking longitudinal displacement of said tissue pick relative to the lumen.

38. The tissue pick according to claim 36 comprising a lock for locking the rotation of said grasping member.

39. The tissue pick according to claim 36 comprising a knob attached to said proximal end of said elongated member for facilitating rotation of said grasping member.

40. The tissue pick according to claim 36 comprising a cam follower cooperating with said helix and adapted for linear movement relative to said helix.

41. The tissue pick according to claim 40, wherein said helix and said cam follower are disposed adjacent said proximal end.

42. The tissue pick according to claim 40, wherein said helix and said cam follower are disposed adjacent said distal end.

43. The tissue pick according to claim 36, wherein said tissue grasping member comprises at least two helically formed opposing prongs, with said prongs grasping an outer portion of tissue upon rotation of said grasping member.

44. The tissue pick according to claim 36, wherein said tissue grasping member comprises at least two spring loaded arc-shaped opposing prongs cooperating with a housing, said tissue grasping member being adapted to be positioned in an extended position, wherein said prongs are disposed in an unbiased opened position substantially outside of said housing, and in a retracted position, wherein said prongs are disposed in a biased closed position substantially inside of said housing.

45. The tissue pick according to claim 36, wherein said elongated member articulates at an angle relative to said outer tube.

46. The tissue pick according to claim 45 comprising a shape-memory inner tube disposed between said outer tube and said elongated member.

47. The tissue pick according to claim 46, wherein said inner tube has an extended position and a retracted position relative to said outer tube, with said inner tube cooperating with said outer tube such that, when said inner tube is in said extended position, said inner tube, together with said elongated member, articulates at an angle relative to said outer tube and when said inner tube is in said retracted position, said inner tube, together with said elongated member, is substantially coaxial with said outer tube.

* * * * *

UNITED STATES PATENT AND TRADEMARK OFFICE
CERTIFICATE OF CORRECTION

PATENT NO. : 6,228,023 B1
DATED : May 8, 2001
INVENTOR(S) : Zaslavsky et al.

It is certified that error appears in the above-identified patent and that said Letters Patent is hereby corrected as shown below:

Column 1,
Line 5, there should be sponsorship information listed as follows:

-- GOVERNMENT RIGHTS
This invention was made with government support under Grant No. R44 DK49878-03 awarded by the National Institutes of Health, National Institute of Diabetes and Digestive and Kidney Diseases. The government has certain rights in the invention. --

Column 5,
Line 54, delete "to".

Column 9,
Line 20, after "about" delete "is" and insert -- its --.

Column 12,
Line 67, delete "claim" and insert -- cam --.

Column 15,
Line 11, delete "Position" and insert -- position --.
Line 15, after "articulates" insert -- at --.

Signed and Sealed this

Thirtieth Day of April, 2002

Attest:

*Attesting Officer*

JAMES E. ROGAN
*Director of the United States Patent and Trademark Office*